United States Patent
Seo et al.

(10) Patent No.: US 6,277,391 B1
(45) Date of Patent: Aug. 21, 2001

(54) COMPOSITION AND METHOD OF TREATING DISEASES AND DISORDERS OF THE PROSTATE

(75) Inventors: Min Hyo Seo; Jae Yong Lee; Jee Hyang Kim; In Ja Choi, all of Taejeon (KR)

(73) Assignee: Samyang Corporation, Seoul (KR)

( * ) Notice: Subject to any disclaimer, the term of this patent is extended or adjusted under 35 U.S.C. 154(b) by 0 days.

(21) Appl. No.: 09/325,894

(22) Filed: Jun. 4, 1999

(30) Foreign Application Priority Data

Jun. 5, 1998 (KR) .......................... KR98-20895

(51) Int. Cl.[7] .................. A61F 2/02; A61K 9/50

(52) U.S. Cl. .................. 424/426; 424/501; 424/502

(58) Field of Search .................. 424/426, 501, 424/502

(56) References Cited

U.S. PATENT DOCUMENTS

| | | |
|---|---|---|
| 4,619,913 | 10/1986 | Luck et al. . |
| 4,675,189 | 6/1987 | Kent et al. . |
| 4,822,610 | 4/1989 | Bush . |
| 4,897,268 | 1/1990 | Tice et al. . |
| 4,946,688 | 8/1990 | Fahim . |
| 5,071,658 | 12/1991 | Fahim . |
| 5,116,615 | 5/1992 | Gokcen et al. . |
| 5,171,217 | * 12/1992 | March et al. .................. 604/53 |
| 5,234,698 | 8/1993 | Fahim . |
| 5,336,263 | 8/1994 | Ersek et al. . |
| 5,434,146 | 7/1995 | Labrie et al. . |
| 5,480,640 | 1/1996 | Morales et al. . |
| 5,599,844 | 2/1997 | Grainger et al. . |

OTHER PUBLICATIONS

J.C. Nickel, Prostatitis: Myths and Realities, Urology, 51 (1998) 362.

E.M. Mearses, Jr., Prostatitis and Related Disorders, in: Walsh, Retik, Stamey and Vaughan, Jr. (Eds), Campbell's Urology 6th Ed., Saunders, Philadelphia 1992, pp. 807–822.

J.E. Fowler, Jr., Prostatitis in: Gillenwater, Grayhack, Howard and Duckett (Eds), Adult and Pediatric Urology 2nd Ed., Mosby–Year Book, St. Louis, 1991, pp. 1395–1423.

J.C. Nickel, New Concepts in the Pathogenesis and Treatment of Prostatitis, Current Opinion in Urology 1992, 2:37–43.

J.C. Nickel, Afridi, Chetner, Fradet, Collins, Klotz, Piercy and Downey, Antibiotic Therapy for Chronic Inflammatory, (NIH Category II/IIIA) Prostatitis, J. Urol. 159 (Suppl. 5) 1998) 272.

D.C. Winningham, Nemoy and Stamey, Diffusion of Antibiotics from Plasma into Prostatic Flud, Nature 219 (1968) 139.

A. Pfau, Prostatitis, A Continuing Enigma, Urol. Clin. North Am. 13 (1986) 695.

(List continued on next page.)

Primary Examiner—Carlos A. Azpuru
(74) Attorney, Agent, or Firm—Thorpe, North & Western llp (57) ABSTRACT

This invention relates to a composition and method for treating diseases and disorders of the prostate such as prostatitis, benign prostatic hypertrophy, and prostate carcinoma. The prostate is treated by intraprostatic injection of a biodegradable sustained release formulation. By injecting the treatment substance directly into the prostate, improved treatment results are obtained with a much lower treatment substance dosage. Additionally, by incorporating the treatment substance into a biodegradable sustained release formulation, the need for frequent repetition of injections is eliminated.

23 Claims, 1 Drawing Sheet

In Vitro Drug Release of Example 1 Microspheres

OTHER PUBLICATIONS

D.J. Lim and A.J. Schaeffer, Prostatitis Syndromes, AUA Update Series 12, (1993) 1.

J.S. Ritter and Charles Lippow, Pathological and Bacteriological Processes Present in Prostatitis and Tissue Reaction to Therapy, J. Urol. 39 (1938) 111.

L. Baert, Mattelaer, and Nollin, Treatment of Chronic Bacterial Prostatitis by Local Injection of Antibiotics into Prostate, Urology 21, (1983) 370.

L. Baert and A. Leonard, Chronic Bacterial Prostatitis: 10 Years of Experience with Local Antibiotics, J. Urol. 140 (1988) 755.

J.F. Jimenez–Cruz, F. B. Tormo and J.G. Gomez, Treatment of Chronic Prostatitis; Intraprostatic Antibiotic Injection Under Echography Control, J. Urol, 139 (1988) 967.

C. Stratton, Fluoroquinolone Antibiotics: Properties of the Class and Individual Agents, Clinical Therapeutics, 14 (1992) 348.

P.A. Todd and D. Faulds, A Reappraisal of its Antimicrobial Activity, Pharmacology and Therapeutic Use, Drugs 42 (1991) 825.

B.A. Cunha, J.B. Comer and M. Jonas, The Tetracyclines, Med. Clin. North Am. 66 (1982) 293.

S.S. Patel, J.A. Balfour and H.M. Bryson, A Review of its Antibacterial Activity, Pharmacokinetic Properties and Therapeutic Efficacy as a Single–Dose Oral Treatment for Acute Uncomplicated Lower Urinary Tract Infections, Drugs, 53 (1997) 637.

J.S. Wolfson and D.C. Hooper, Treatment of Genitourinary Tract Infections with Fluoroquinolones: Activity in Vitro, Pharmacokinetics, and Clininical Efficacy in Urinary Tract Infections and Prostatitis, Antimicrobial Agents and Chemotherapy 33 (1989) 1655.

M.G. Bergeron, The Pharmacokinetics and Tissue Penetration of the Fluoroquinolones, Clinical and Investigative Medicine, 12 (1989) 20.

G.J. Davis, McKenzie, Toxicologic Evaluation of Ofloxacin, Am. J. Medicine 87 (1989) 43S.

C. Tallarigo, L. Comunale, R. Baldassare, G. Novella, Ofloxacin: Evaluation of Distribution in the Prostate Clinical Efficacy in Bacterial Prostatitis, Clinical Trials Journal, 26 (1989) 233.

K.G. Naber, Use of Quinolones in Urinary Tract Infections and Prostatitis, Reviews of Infectious Diseases, 11 (1989) S1321.

K. Suzuki, H. Tamai, Y. Naide, K. Ando and R. Moriguchi, Laboratory and Clinical Study of Ofloxacin in Treatment of Bacterial Prostatitis, Hinyokika Kiyo 30 (1984) 1505.

J.C.D. Png, E. Tan, K.T. Foo, M.K. Li, C. Cheng and I.R. Rekhraj, A Comparative Study of the Distribution of Ofloxacin and Ciprofloxacin in Prostatic Tissues after Simultaneous Oral Ingestion, British Journal of Urology 79 (1997) 781.

S. Saivin and G. Houin, Clinical Pharmacokinetics of Doxycycline and Minocycline, Clinical Pharmacokinetics 15 (1988) 355.

B.A. Cunha and S.M. Garabedian–Ruffalo, Tetracyclines in Urology: Current Concepts, Urology 36 (1990) 548.

W.R. Fair and J.J. Cordonner, The pH of Prostatic Flud: A Reappraisal and Therapeutic sImplications, J. Urol. 120 (1978) 695.

* cited by examiner

COMPOSITION AND METHOD OF TREATING DISEASES AND DISORDERS OF THE PROSTATE

CROSS REFERENCE TO RELATED APPLICATIONS

This application claims priority under 37 C.F.R. 119 from earlier filed application No. KR98-20895, filed Jun. 5, 1998, in the Korean Patent Office.

THE FIELD OF THE INVENTION

The present invention relates generally to a method of treating diseases and disorders of the prostate such as prostatitis, benign prostatic hypertrophy, and prostate carcinoma. More particularly, it concerns making treatment by injecting a biodegradable sustained release formulation directly into the prostate.

BACKGROUND OF THE INVENTION

Prostate diseases such as prostatitis, benign prostatic hypertrophy, prostatodynia, and prostate carcinoma afflict many adult males. The largest population of men stricken with prostate problems are those over age fifty. However, inherited prostate problems can appear in much younger men.

Prostatitis is generally an inflammation of the prostate gland and the surrounding tissue. Several causes of inflammation are known and have been categorized by the National Institute of Health. Category I is recognized as acute bacterial prostatitis. Category II is chronic bacterial prostatitis. Category III includes chronic abacterial prostatitis and CPPS (Chronic Pelvic Pain Syndrome). Category IIIA is inflammatory CPPS, and Category IIIB is non-inflammatory CPPS. Finally, Category IV encompasses asymptomatic inflammatory prostatitis.

Category I, acute bacterial prostatitis, has been quite effectively managed in the past using a wide spectrum of antibiotics. Category II, chronic bacterial prostatitis, is most often treated with higher potency drugs for management such as Quinolone or Trimethoprim therapy for as long as needed. Attempts at treating Category IIIA, inflammatory CPPS, have been made using a wide variety of antibiotic and anti-inflammatory agents.

Administration of treatment substances through the bloodstream has been less than satisfactory in treating prostate diseases. Large doses of treatment substance have been required for effective treatment. Therefore, it is now believed that a filtering barrier exists between the prostate and the body's blood supply which prevents treatment substances from entering the prostate. The problematic effect of this barrier is two fold. First, the barrier prevents most of the treatment substance dosage from entering the prostate and having a therapeutic effect. Second, the barrier mandates extremely high doses of the treatment substance in order to have a therapeutic effect. Since most of the drug is not allowed into the prostate it remains in the body's general circulation. This results in many undesirable side effects.

In an attempt to reduce the need of high doses of strong antibiotics and other treatment substances, many urologists have turned to injecting treatment substances directly into the prostate. Although this procedure has yielded greater therapeutic results at much lower doses, frequent repetition of injections is generally required to obtain adequate treatment results. This frequent injection repetition causes much pain, discomfort, and inconvenience to the patient.

Benign prostatic hypertrophy is a condition where the prostate over-grows or becomes enlarged. Prostate growth is controlled by androgen receptors found in the prostate gland. When the androgen receptors are stimulated by 5 α-dihydrotesterone (DHT), they cause the prostate to grow. DHT is produced by an enzymatic conversion of testosterone in the prostate.

The main treatments for benign prostatic hypertrophy have been drug therapy and surgery. Transurethral resection of the prostate (TURP) is the most widely used surgical treatment procedure. The most widely used drug therapy has been the bloodstream administration of an α-blocker such as terazosin or doxazosin. Additionally, bloodstream administration of a 5 α-reductase inhibitor such as finasteride has been used. These drugs, however, often have the undesirable side effects of postural hypotension or impotence, and decreased libido. Additionally, these drugs must be continually administered for the duration of the patient's life in order to prevent a return of the problem.

One new method of treating benign prostatic hypertrophy is the intraprostatic injection of a collagenase, hyaluronidase mixture. This mixture effectively dissolves prostatic tissue which has the ultimate effect of shrinking the prostate. However, since this treatment does nothing to prevent further prostate growth, the treatment must reapplied as frequently as new prostate growth demands.

Prostate carcinoma is a neoplasm which most frequently affects men over 50 years old and is a leading cause of cancer deaths in men. Radical prostatectomy or surgical removal of the prostate, and radiation therapy are the most common treatment methods for prostate carcinoma. However, radical prostatectomy often results in impotence and urinary incontinence. Radiation therapy, while having a somewhat lower cure rate than surgery, is generally well tolerated. However, radiation therapy has also been known to produce impotence, incontinence, cystitis, and proctitis.

In addition to surgery and radiation therapy, other methods for treating prostate carcinoma have been employed. One such method is the intramuscular or subcutaneous injection of a sustained release depot formulation which contains LHRH agonists. This method is not without adverse side effects, such as prolonged systemic exposure to high doses of the formulation. Another, more recent treatment method is the intraprostatic or intralesional injection of alpha interferon. This method too has the unfortunate requirement of frequent repetitive injections over a substantial period of time.

In view of the foregoing, a method of treating prostate diseases and disorders which minimizes adverse side effects as well as a patient's pain and discomfort is highly desirable. Further, a method of treatment which allows effective therapeutic results with lower doses of the treatment substance is desirable. Additionally, a method of treatment which produces a sustained delivery of the treatment substance over long periods of time is desirable.

OBJECTS AND SUMMARY OF THE INVENTION

It is therefore an object of the present invention to provide an injectable pharmaceutically acceptable composition for the treatment of prostatic diseases and disorders, including but not limited to, prostatitis, benign prostatic hypertrophy, and prostate carcinoma.

It is an additional object of the present invention to provide a method for treating diseases of the prostate which requires a significantly smaller dose than the presently known treatments, but which yields similar or better treatment results.

It is yet another object of the present invention to provide a method for treating prostate diseases and disorders with an intraprostatic injection which does not need to be frequently re-administered or repeated.

The above objects and others not specifically recited are realized in a few specific illustrative embodiments of an injectable treatment composition. The treatment composition generally includes at least one therapeutically effective substance for treatment of prostatic diseases and disorders. It may however contain a combination of these substances.

When the specific disease or disorder is prostatitis, this therapeutically effective substance is selected from the group consisting of antibiotics, anti-inflammatory drugs, and mixtures thereof. Additionally, when the specific disease or disorder is benign prostatic hypertrophy, the therapeutically effective substance is selected from the group consisting of α-blockers, 5 α-reductse, cytotoxic drugs, anti-angiogenetic drugs, and mixtures thereof. Finally, when the specific disease or disorder is prostate carcinoma, the therapeutically effective substance is an anticancer agent. This anticancer agent is often a member selected from the group consisting of alkylating agents, cytotoxic antibiotics, steroid hormones, vinca alkaloids, anti-angiogenetic agents, and mixtures thereof.

Whatever the specific therapeutically effective substance, it will be combined with a biodegradable polymer to form microspheres. The therapeutically effective substance will generally comprise about 10% to 50% w/w of the total microsphere mass. This amount is considered adequate to provide a sustained release rate yielding therapeutically effective treatment results. The rest of the microsphere mass is comprised of the biodegraded polymer which is generally an aliphatic polyester of a hydroxy acid. Most often, this polymer is a member selected from the group consisting of: polylactic acid(L,DL), polyglycolic acid, poly(lactic-co-glycolic) acid, poly(orthoesters), poly(p-dioxanone), poly(alpha hydroxy butyric acid), and their copolymers with polyethylene oxide or polypropylene oxide, and mixtures thereof. The microspheres produced in this manner are generally 1 $\mu$m–100 $\mu$m and comprise the main treatment composition.

The final component in the pharmaceutically acceptable composition is a liquid within which the microspheres are suspended. Normally about 1 ml to 5 ml of liquid is used to produce a single injection. This liquid is most often a sterile diluent which may contain pharmaceutically acceptable excipients for increasing drug stability and drug release control. Sometimes the sterile diluent has sol-gel properties, and may even be a substance which exists as a liquid before injection, and a gel at human body temperatures. Suspension of the microspheres in this manner enables them to be injected intraprostatically.

A method of treating diseases and disorders of the prostate using the above mentioned pharmaceutically acceptable composition is additionally provided. This method generally requires the steps of: selecting a desired therapeutically effective treatment substance, selecting a desired biodegradable polymer, combining the therapeutically effective substance and the biodegradable polymer to form microspheres, suspending the microspheres in a liquid, loading the microsphere containing liquid into a syringe, and injecting the same directly into the prostate. Additional steps in the method may include agitating the microsphere containing liquid to achieve an even microsphere disbursement, and injecting the microsphere containing liquid into the prostate through a transurethral, transrectal, or transperineal route.

The method of treatment may comprise only a single injection of the above described pharmaceutical compositions, or injections may be re-administered as needed until a satisfactory therapeutic treatment result is obtained.

Additional objects and advantages of the invention will be set forth in the description which follows, and in part will be apparent from the description, or may be learned by the practice of the invention without undue experimentation. The objects and advantages of the invention may be realized and obtained by means of the instruments and combinations particularly pointed out in the appended claim.

BRIEF DESCRIPTION OF THE DRAWINGS

The above and other objects, features and advantages of the invention will become apparent from consideration of the subsequent detailed description presented in connection with the accompanying drawings in which.

DETAILED DESCRIPTION OF THE INVENTION

For the purposes of promoting an understanding of the principles in accordance with the invention, reference will now be made to specific embodiments thereof, and specific language will be used to describe the same. It will nevertheless be understood that no limitation of the scope of the invention is thereby intended. It is of course understood, that any alterations and further modifications of the illustrated method, or any additional applications of the principles of the invention as described herein, which would normally occur to one skilled in the relevant art and in possession of this disclosure, are to be considered within the scope of the invention claimed.

The present invention contemplates a method of treating diseases and disorders of the prostate by injecting biodegradable microspheres containing a treatment substance directly into the prostate. The injection of the treatment substance directly into the prostate allows the achievement of therapeutic effects at much lower doses. Additionally, the use of microspheres allow for a sustained release of the treatment substance over a long period of time which eliminates the need for frequent repetition of injections.

1. Biodegradable Microsphere Delivery System

Microspheres are generally fine spherical particles with a diameter of less than 1000 $\mu$m, which are comprised of a polymer matrix containing a drug. There are two general types of microspheres. The first type are homogeneous or monolithic microspheres. These microspheres utilize a solid dispersion of the drug which is dissolved or dispersed throughout the polymer matrix of the microsphere. The second type are reservoir type microspheres, or microcapsules. These microspheres provide an outer polymer matrix, generally in the mononuclear or polynuclear state, which micro-encapsulate the drug.

Biodegradable microsphere delivery systems can provide not only a controlled drug release, but can also be used to target drug delivery to specific sites of action. This gives the administrator to the ability to increase therapeutic effects during treatment while reducing side effects. Additionally, microspheres are easily injected via subcutaneous, intramuscular, and intralesional routes, allowing either local or systemic delivery. Therefore when used locally, therapeutically effective results can be obtained by much lower doses of the treatment substance.

Polymers used in manufacturing microspheres are preferably selected from polylactic acid(L,DL), polyglycolic acid, poly(lactic-co-glycolic) acid, poly(orthoesters), poly (p-dioxanone), poly(alpha hydroxy butyric acid), and their copolymers with polyethylene oxide or polypropylene oxide, or a mixture of any of the above. Ultimately, selection of the specific polymer depends on the drug to be delivered and the desired rate of release. Release rate is determined by the combination of the drug to be delivered, and the specific characteristics of the selected polymer (i.e. species, molecular weight, and monomer ratio).

There are four major classifications of methods for producing microspheres with the above listed biodegradable polymers. These method classes include: 1) liquid solvent evaporation methods; 2) phase separation methods; 3) interfacial reactions methods; and 4) physical methods.

Each of the above listed general method classes encompasses several specific methods or protocols. The class of liquid solvent evaporation includes various emulsion methods such as O/W, O/O, W/O/W, and (S/O)/W, etc. Included in the class of phase separation methods are aqueous and organic phase separation processes, melt dispersion, and spray drying. Interfacial reaction methods include interfacial polymerization, in situ polymerization, an chemical vapor depositions. The physical methods class includes fluidized bed spray coating, electrostatic coating, and physical vapor deposition.

Microspheres ranging in diameter from about 0.1 $\mu$m to about 250 $\mu$m are capable of being injected through an 18 gauge needle. However, in order to reduce patient's discomfort during injection a finer needle of at least 23 gauge is preferable. In order to be easily injected through a 23 gauge needle, microspheres need to have a diameter smaller than 75 $\mu$m. Therefore fabrication techniques yielding microspheres in this size range are most desirable. Alternatively, microspheres can be sieved to separate out those which are too large.

2. Method for Treating Prostatitis

The most common pathogens of prostatitis are gram-negative bacteria such as *Escherichia coli,* Klebsiella, Proteus spp., and other Enterobacteriaceae. Gonococcal, Parasitic, Viral, Tubuerculous, and Fungal pathogens are generally uncommon. Additionally, Enterococcus, *Ureaplasma urealyticum,* and *Chlamydia trachomatis,* are some of the pathogens suspected to cause nonbacterial prostatitis, however to date there is little proof of their involvement.

For the treatment of prostatitis, a broad range of antibiotics and anti-inflammatory agents have been used. Because of nature of the above mentioned pathogens, antibiotics which show a wide spectrum against them are usually preferred for treatment. Specifically, some of the drugs are trimethoprimsulfamethoxazole, minocycline, doxycycline, cefazolin, carbenicillin, erythromycin, cephalexin, kanamycin, tobramycin, gentamicin, and thiamphenicol. More recently, however, fluoroquinolone antibiotics such as ciprofloxacin, norfloxacin, ofloxacin, and levofloxacin have recently proven successful in eradicating the organisms which cause acute or chronic prostatitis. The floroquinolones are particularly effective because they penetrate prostatic tissue very well, and are highly effective against most of the organisms likely to be encountered, including gram-positive rods and Pseudomonas aeruginosa. Ofloxacin has been particularly effective when used to treat *Chlamydia trachtomatis* infections.

All of the above mentioned antibiotics can be encapsulated and effectively delivered using the biodegradable microspheres of this invention. However, the antibiotics which have low minimum inhibitory concentrations (MIC) against the pathogens of prostatitis, such as the fluoroquinones, are more desirable.

Though dependent upon the kind of antibiotics and the route of administration, a conventionally recommended duration of antibiotic therapy for treating prostatitis ranges from 1 to 3 months. Recommended dosage also varies with the kind of antibiotics selected for treatment. For example, in the case of ofloxacin, 300 mg PO b.i.d., administered orally or intravenously, for 6 weeks is generally recommended. Following this regimen, the total amount of ofloxacin delivered into the body during one month of therapy is about 18 g. However, test results have shown that at the end of this regimen, ofloxacin concentrations in the prostate range only from 1–4 $\mu$g/g. Thus, because the drug is administered systemically, most of it does not work to treat prostatitis. It is currently believed that this is due to the blood prostate barrier mentioned earlier.

The method of the current invention is to intraprosatically inject biodegradable microspheres containing antibiotics effective for the treatment of prostatitis. By using this method, the same or higher prostatic tissue concentrations of the antibiotic are obtained when using only $\frac{1}{1000}$ of the dosage amount used in systemic administration. Anti-inflammatory and anticholinergic agents may also be delivered by the method of this invention with similar results.

3. Method for Treating Benign Prostatic Hypertrophy

Benign Prostatic Hypertrophy occurs when the prostate enlarges or swells. This often occurs due to the body's aging process rather than infection. Androgen receptors located on the prostate control prostatic growth. Stimulation of these androgen receptors with 5 $\alpha$-dihydrotestosterone (DHT) fosters prostate growth. The prostate typically remains stable in weight and histological characteristics for around 25 years. When a man reaches about age 50, a second spurt of growth begins. This second growth phase originates in the periurethral area of the gland as a localized proliferation of cells.

As mentioned above, administration of $\alpha$-blockers such as 5 $\alpha$-reductase inhibitor is suggested drug therapy for the treatment of Benign Prostatic Hypertrophy (BPH). As also mentioned above, these drugs may cause postural hypotension, or impotence, as well as decreased libido. Unfortunately must be continually administered for the duration of the patient's life in order to prevent a relapse from occurring. However, the androgen receptors upon which these drugs act reside in the prostate. Therefore, these drugs may be delivered using the method of the current invention. Delivering these drugs via biodegradable microspheres which are intraprosatically injected localizes delivery and greatly reduces the dosage amount needed to obtain therapeutic effects. Therefore, the above mentioned adverse side effects are almost completely eliminated.

BPH is caused by proliferation and enlargement of prostatic cells. Therefore, shrinking enlarged prostate cells, and inhibiting further proliferation are a desirable means of affording a patient relief from the symptoms of already existing BPH. To this end, other kinds of drugs have been suggested for treatment such as cytotoxic and anti-angiogenetic drugs. These drugs have a necrotic, or shrinking effect on prostatic cells.

The origination of BPH is believed to arise from an inner set of prostatic ducts and glands that reside within or adjacent to the urethral wall. Because of this unfavorable position, treatment the method of the current invention is most effective. Although intraprostatic injection alone would suffice, it does create the need for additional injections as prostate growth demands. The classes of drugs contemplated for BPH treatment in this invention are: 1) conventional drug treatment of BPH, including finasteride, terazosin, doxazosin, etc.; 2) cytotoxic agents, including actinomycin D, doxorubicin, mitomcin, mithramycin, bleomycin, minocylcine, etc.; 3) anti-angiogenetic drugs, including TGF-β, interferon α-2a, TNF-α, angiostatin, fumagillin, minocycline, herbimycin A, ovalicin, 2-methoxyoestradiol, sumarin, protamine, thalidomide, paclitaxel, etc.

4. Method for Treating Prostate Cancer

The method of the current invention is especially well suited for treatment of prostate cancer or carcinoma. Anti-cancer agents may be loaded into microcapsules and injected directly into the prostate. Confinement of the treatment agent to a small localized area, and reduction of the required dosage amount, are extremely desirable considering the generally bad side effects of anticancer agents when administered systemically.

The majority of anticancer drugs can be used in the current invention. Included among them are: 1) alkylating agents such as mustine, cyclophosphamide, chlormbucin, busulphan, and cisplatin; 2) cytotoxic antibiotics such as actinomycin D, doxorubicin, mitomycin, mithramycin, and bleomycin; 3) steroid hormones like glucocorticoids, oestregens, anti-oestrogens, and androgens; 4) vinca alkaloids such as vinblastine and vincrisitne; 5) anti-angiogenetic agents such as TGF-β, interferon α-2a, TNF-α, angiostatin, fumagillin, minocycline, herbimycin A, ovalicin, 2-methoxyoestradiol, sumarin, protamine, thalidomide, and paclitaxel; and 6) other miscellaneous drugs such as methotrexate, fluorouracin, mercaptoputine, prednisone, and tamoxifen. Drugs can be delivered singly or in combinations.

5. Method of Injection

For intraprostatic injection, microspheres are suspended in pharmaceutically acceptable liquid compositions. A typical matrix for the liquid composition is sterile water since it is the vehicle for all natureal body fluids. Additionally, the water may contain various excipients for different purposes such as suspending agents like gelatin, pectin, sodium, carboxymethylcellulose, or polyeethlyene glycol. Additionally, buffers such as acetic acid, citirica acid, lactica acid, potassium phosphate, sodium phosphate, sodium bicarvonate, tartaric acid, and their salts may be included. Antimicrobial preservatives like benzyl alcohol, metacresol, methylparaben, and phenol may be included as excipients. Emulsifiers such as polysorbate 80, propylene glycol, povidone, sorbitan monopalmitate, may be included as well as tonicity modifiers like glycerine, lactose, mannitol, dextrose, sodium chloride, and sorbitol. Finally, local anesthetics may be included in the suspension solution such as lidocaine hydrochloride, procaine hydrochloride, and menzyl alcohol.

Microspheres may be suspended in mediums other than water which can help increase efficiency such as insitu gel formulations. For example, Poloxamer 188 becomes a clear solution when dissolved in water with a temperature of below 5° C. The mixture will again become a gel at a temperature around that of a human body. Therefore, if microspheres are suspended in an aqueous cold Poloxamer 188 solution, the mixture may be freely injected into the body. Upon entry into the body the solution once again becomes a gel. Utilizing the gel in to suspend the microspheres in this manner greatly contributes to control and accuracy in obtaining the desired sustained drug release pattern. Additionally, drugs can be dissolved directly into the gel solution in addition to the microspheres. This allows the administrator to deliver two drugs with independent release patterns. Often the drug dissolved in the gel solution will be the same as the one contained in the microspheres. This procedure is advantageous, as the drug contained in the gel will be delivered more quickly, and the drug in the microspheres more slowly. This is one method of maximizing effectiveness of treatment, because an initial high dosage is quickly delivered, followed by the sustained release of the same treatment substance over a desired period of time.

The general injection method is as follows. First, using a syringe with a needle equip for spinal injection, 1 to 5 ml of the desired liquid composition is withdrawn and then injected into a vial containing the microspheres to be delivered. Next, the vial containing the liquid composition and the microspheres is shaken vigorously to ensure thorough dispersion of the microspheres throughout the liquid composition and create a uniform suspension. The entire contents of the vial then are withdrawn into the syringe and immediately injected into the prostate via transurethral, transrectal, or transperineal injection methods.

Treatment parameters will vary depending on the nature of the specific affliction, the general health and age of the patient, etc. The number of injections and the interval between them depends also upon the disorder, the treatment substance to be used, the release profile of the microspheres, and the patient's progress. In most prostatitis cases a single injection will suffice. In other cases, an injection may be administered weekly, biweekly, monthly, bimonthly, or trimonthly.

The amount of microspheres contained in each injection depends on the characteristics of the drugs being delivered and the specific malady being treated. Microsphere amount will also depend on the drug contents of the microspheres, and the finite size of the prostate. Injection of the suspension is best limited to less than 5 ml, and more preferably to less than 2 ml. Therefore suspension of no more than 150 mg of microspheres in the liquid composition is desired, and suspension of less than 50 mg of microspheres is best.

EXAMPLES

Preparation of Microspheres

Example 1

1.4 g of poly-D,L-lactic acid (molecular weight about 8,000 by GPC) was dissolved in 2 ml of dichloromethane. 0.6 g of finely crushed ofloxacin was added to the above solution and mixed for 2 hours to form a uniform suspension. The resultant suspension was then poured into 150 ml of 5% w/w aqueous solution of polyvinyl alcohol containing 0.1% silicon colloid and stirred for 1 hour at 5° C. to form an emulsion. Next, 1,000 ml of distilled water was added to the emulsion and stirred for 1 hour at room temperature to remove the dichloromethane and produce microspheres. The microspheres were then centrifuged, washed with water, and lyophilized. Average particle size obtained by this method was about 40 μm and drug content was 29% w/w.

Example 2

1.4 g of poly-D,L-lactic acid (molecular weight about 10,000 by GPC) was dissolved in 2 ml of dichloromethane.

0.6 g of finely crushed ibuprofen sodium salt was then added to the above solution and mixed for 2 hours to form a uniform suspension. The resultant suspension was poured into 150 ml of 4% w/w aqueous solution of polyvinyl alcohol containing 0.05% 2-octanol and stirred for 90 minutes at 5° C. to form an emulsion. Next 1,000 ml of distilled water was added to the emulsion and stirred for 1 hour at room temperature to remove the dichloromethane and to obtain microspheres. The resultant microspheres were then centrifuged, washed with water, and lyophilized. The average particle size of the microspheres obtained was about 45 μm and the drug content was 28% w/w.

Example 3

1.4 g of poly(D,L-lactic-co-glycolic) acid (molecular weight of about 14,000 by GPC, LA/GA=75/25) was dissolved in 2 ml of dichloromethane. 0.6 g of finely crushed minocycline HCL was then added to the above solution and mixed for 3 hours to form a uniform suspension. The resultant suspension was poured into 200 ml of 5% w/w aqueous solution of polyvinyl alcohol and stirred for 1 hour at 5° C. to form an emulsion. Next, 1,500 ml of distilled water was added to the emulsion and stirred for 1 hour at room temperature to remove the dichloromethane and to make microspheres. The resultant microspheres were centrifuged, washed with water, and lyophilized. The average particle size of the microspheres obtained in this manner was about 35 μm, and the drug content was 23% w/w.

Example 4

1.6 g of poly-D,L-lactic acid (molecular weight of about 8,000 GPC) and 0.4 g of paclitaxel were dissolved in 2 ml of dichloromethane at 5° C. The resultant solution was poured into 200 ml of 5% w/w aqueous solution of polyvinyl alcohol containing 0.1% silicon colloid and stirred for 1 hour at 5° C. to form an emulsion. Then 1,000 ml of distilled water was added to emulsion and stirred for 1 hour at room temperature to remove dichlormethane and to get microspheres. The resultant microspheres were centrifuged, washed with water, sieved with a 200 mesh s/s sieve, and then lyophilized. The average particle size of the microspheres obtained was about 40 μm and the drug content was 18% w/w.

Example 5

1.4 g of poly(D,L-lactic-co-glycolic) acid (molecular weight about 30,000 by GPC, LA/GA=50/50) was dissolved in 3 ml of acetonitrile. 0.6 g of finely crushed ampicillin sodium salt was added to the above solution and mixed for 2 hours to form a uniform suspension. The resultant suspension was then poured into 200 ml of mineral oil containing 3 % w/w of sorbitan monooleate and stirred for 3 hours with an increasing temperature gradient rising from 25° C. to 50° C. to form an emulsion and remove the acetonitrile. The resultant microspheres were centrifuged, washed with heptane, and then dried. The average particle size of the microspheres obtained was about 40 μm and the drug content was 21% w/w.

Example 6

0.8 g of poly-D,L-lactic acid (molecular weight about 8,000 GPC) and 0.2 g of finasteride were dissolved in 1 ml of dichloromethane at 5° C. The resultant solution was poured into 100 ml of 5% w/w aqueous solution of polyvinyl alcohol and stirred for 1 hour at room temperature to remove the dichloromethane and to get microspheres. The resultant microspheres were centrifuged, washed with water, sieved with a 200 mesh s/s sieve, and lyophilized. The average particle size of the microspheres obtained was about 38 μm, and the drug content was 17% w/w.

Example 7

1.4 g of poly(D,L-lactic-co-glycolic) acid (molecular weight about 37,000 GPC, LA/GA=50/50) and 0.6 g of adriamycin were dissolved in 2 ml of dichloromethane at 5° C. The resultant solution was poured into 200 ml of 5% w/w aqueous solution of polyvinyl alcohol and stirred for 1 hour to form an emulsion. Then 1,000 ml of distilled water was added to the emulsion and stirred for 1 hour at room temperature to remove the dichloromethane, and to obtain microspheres. The resultant microspheres were centrifuged, washed with water, sieved with a 200 mesh s/s sieve, and lyophilized. The average particle size of the microspheres obtained was about 40 μm, and the drug content was 24% w/w.

Example 8

1.4 g of poly(D,L-lactic-co-glycolic) acid (molecular weight about 14,000 by GPC, LA/GA=75/25) was dissolved in 2 ml of dichloromethane. 0.6 g of finely crushed terazosin HCL was added to the above solution and mixed for 2 hours to create a uniform suspension. The resultant suspension was then poured into 250 ml of 5% w/w aqueous solution of polyvinyl alcohol and stirred for 1 hour at 5° C. to form an emulsion. Next, 1,500 ml of distilled water was added to the emulsion and stirred for 1 hour at room temperature to remove the dichloromethane and to get microspheres. The resultant microspheres were centrifuge, washed with water, and lyophilized. The average particle size of the microspheres obtained was about 42 μm, and the drug content was 22% w/w.

Preparation of Aqueous Vehicles for Injection of Microspheres

Example 9

Polysorbate 80, Sodium carboxymethylcellulose of low viscosity, D-mannito, and lidocaine hydrochloride were dissolved in water for injection.

| Substance | Amount |
| --- | --- |
| Polysorbate 80 | 200 mg |
| Sodium carboxymethylcellulose | 1 g |
| D-mannitol | 10 g |
| Lidocaine hydrochloride | 2 g |
| Water for injection | 200 g |

Other aqueous vehicles are possible for in situ gel formulation. For example dissolution of 60 g of Poloxamer 188, and 2 g of procaine hydrochloride in 200 ml of water at 5° C.

The microspheres of Example 1–8 were freely injected through a 23 gauge needle when dispersed in the above aqueous vehicle and in the low temperature Poloxamer solution.

In Vitro Drug Release of Microspheres

Example 10

Figure 1:
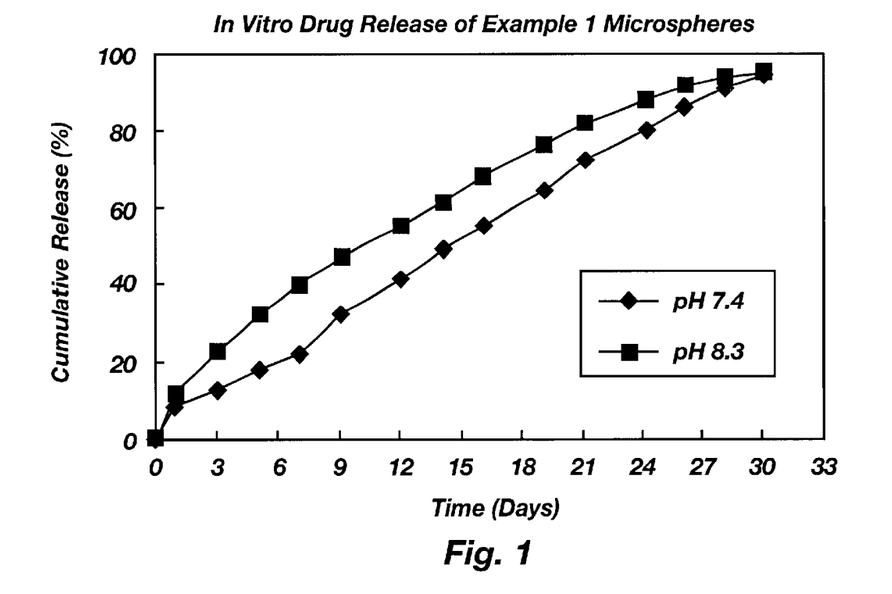
FIG. 1 is a graphical representation of an in vitro release profile of oflaxacin containing microspheres produced in accordance with the method described below in Example 1.

Referring now to FIG. 1, a release profile is shown for drug released from the microspheres over a 30 day period.

The graph results from an in vitro release study performed at two different pH levels. A pH level of 7.4 was selected to represent the pH of an uninflamed human prostate, and the pH level of 8.3 was chosen to represent the pH of an inflamed human prostate. The in vitro study was performed at a temperature of 37° C., and 50 rpm. Approximately 25 mg of microspheres were suspended in a plastic tube containing 10 ml of a solution having a pH of 7.4, 0.01 M PBS, containing 0.02% Tween 80. Additionally, another 25 mg of microspheres were suspended in a plastic tube containing 10 ml of the above solution tris-buffered to a pH of 8.3. The entire medium of both suspensions was collected at designated sampling times, and each replaced with 10 ml of fresh medium. Each collected medium was filtered and analyzed by HPLC.

FIG. 1 shows that by day number 30 nearly all of the drug contained in the microspheres had been delivered. Additionally, microspheres contained in a medium of 8.3 pH deliver the drug more quickly than that at the lower pH of 7.4.

Example 11

Figure 2:
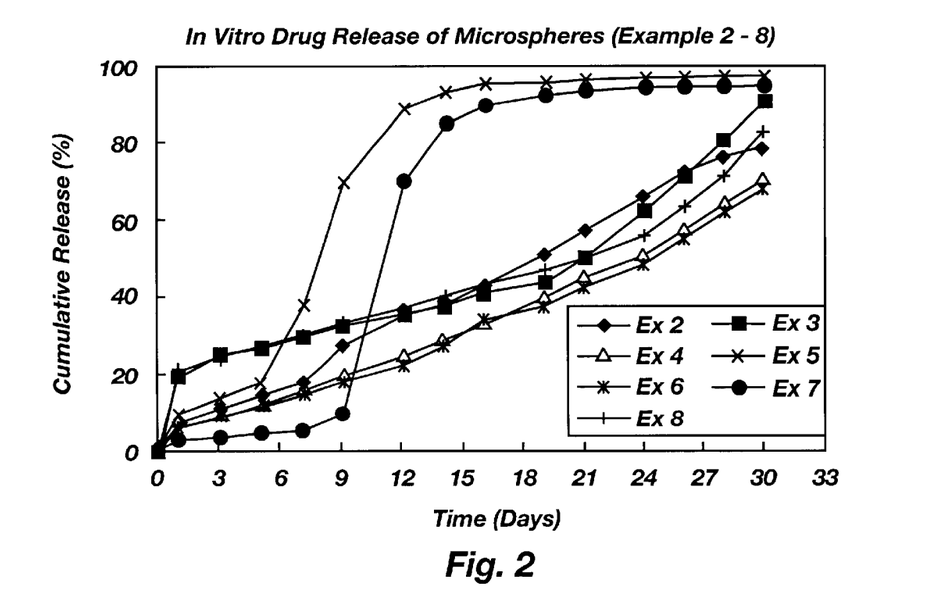
FIG. 2 is a graphical representation of the in vitro release profiles of other drug containing microspheres produced in accordance with the methods described below in Examples 2–8.

Referring now to FIG. 2, there is shown the release pattern of microspheres fabricated according to the methods described in the above illustrated examples 2–8. This in vitro release experiment was performed at a temperature of 37° C., and 50 rpm. Approximately 20 mg of each of the different microspheres made by the above methods 2–8, were suspended in separate plastic tubes or flasks, each containing 10–100 ml of a solution having a pH of 7.4, 0.01 M PBS, containing 0.02% Tween 80. The entire medium of each tube or flask was collected at designated sampling times, and replaced with 10 ml of fresh medium. Each collected medium was filtered and analyzed by HPLC.

FIG. 2 shows the profile of release for each microsphere over an approximately 30 day period. One particularly interesting result is the 2 week release of the drugs incorporated into microspheres made of poly(D,L-lactic-co-glycolic) acid (LA/GA=50/50), and the biphase release pattern they displayed.

In Vivo Evaluation of Ofloxacin Loaded Microspheres

In this in vivo evaluation, 6 healthy male mongrel dogs of about 24 months in age, and body weight of 30 kg were tested.

Example 12

Control Group (Oral Administration)

100 mg ofloxacin tablets were used for oral administration. 2 dogs were treated with 200 mg b.i.d. for 14 and 19 consecutive day periods.

On the sampling day, 200 mg of ofloxacin tablets were administered at 9 a.m. and another 200 mg were administered at 12 p.m. to elevate the level of the drug in the blood. The operation to collect the prostate was performed at 2 p.m.

The dog was anesthetized with relatively high dose of xyaline 1.5 mg/kg and 30 mg/kg of ketamine hydrochloride. Once anesthetized, 10 ml of blood was collected from the dog's femoral vessel, and a vascular line was maintained. A lower abdominal mid-line incision was made just next to the dog's penis into the peritoneal cavity. The prostate was removed en bloc including the bladder neck and infraprostatic posterior urethra. Following removal of the prostate, the dog was euthanized with an overdose infusion of magnesium sulfate. The periprostatic tissues were completely removed and the prostate was divided in half alon the median groove. Each lobe of the prostate was then divided into 9 segments each of which was again divided in half. One of each of these halves was then fixed with 10% formalin for pathological study and the other half was frozen in a deep freezer until a tissue evaluation could be performed.

Example 13

Experimental Group 4 dogs were treated with a single intraprostatic injection containing 40 mg of ofloxacin loaded microspheres. The microspheres had been fabricated by the method illustrated above in example 1. Sampling of the dog's prostates took place at weeks 1,2,3, and 4 following the injection. The below described procedure was used to administer the intraprostatic injection to each dog.

The dog was maintained in that NPA (non per os) state from 9:00 p.m. the day before the operation. At the commencement of the surgery, each dog was anesthetized with a mixture of 5 mg atropine, 1 mg/kg xyaline, and 15 mg/kg ketamine HCL. Immediately following anesthetization, 10 ml of blood was drawn from the anterior leg and an intravenous line was there maintained. Delivered through the intravenous line was 50 drops per minute of a 5% Hartman-dextrose solution. Next the lower half of the abdomen was shaved, including the hair covering the penis and upper thigh. Following a potadine washing, painting and draping, a lower abdominal mid-line incision was made parallel to the penis from about 5 cm above the penis tip to the penile root. After division of subcutaneous tissue, the rectus sheath was incised and undermined with mexembaum. The urine filled bladder was exposed and the bladder neck and prostate were palpitated. The traction of the lower bladder was made with an Allis clamp without damaging any periprostatic tissue and the microsphere suspension was injected into the parenchyme of the left lobe of the prostate. The incision was then closed layer by layer up to the outer epidermis. The duration of each operation was approximately one and a half hours. At the end of the specified time period, each dog was sacrificed and the prostates collected in the manner described above for the control group.

Example 14

Assay of Drug Concentration in Serum (blood) and Prostatic Tissue

A sample of prostatic tissue was weighed and homogenized using PowerGen 1800D, Fisher Scientific, Pittsburgh, U.S.A. with 4.3 ml of PBS (0.1 M, pH 7.0) and the homogenate was centrifuge at 1600 g for 10 minutes. The supernatant was decanted and re-centrifuged before extraction for HPLC analysis.

For HPLC analysis, 50 $\mu$l of internal standard and 3 ml of dichloromethane were added to 800 $\mu$l of serum or tissue supernatant, and agitated for 15 minutes. The mixture was then centrifuged at 1600 g for 10 minutes. Following the centrifugation, 4 ml of the dichloromethane was extracted and dried in a nitrogen stream. The residue was then dissolved in 1 ml of mobile phase and 10 $\mu$l of the final sample was injected into the HPLC system. Standard solutions of 0.5–100 $\mu$g/g of ofloxacin were prepared. An internal standard of enoxacin was prepared in 0.1 M PBS (pH 7.0).

Ofloxacin levels were obtained from the serum and prostate specimens, and prostatic tissue drug levels were calculated. Results were expressed in drug concentration per gram of prostate tissue.

TABLE 1

Serum and tissue concentrations of ofloxacin

| Method of Administration | Serum Conc. ($\mu$g/ml) | Prostatic Tissue Concentration ($\mu$g/g) Average ± S.D. (range) | |
|---|---|---|---|
| Consecutive Oral Administration | | | |
| 2 Weeks | 3.5 | 9.4 ± 1.3 (7.4–10.8)[a] | |
| 3 Weeks | 6.1 | 7.4 ± 1.4 (6.2–9.9)[a] | |
| Single Intraprostatic | | Left Lobe[b] | Right Lobe[b] |
| Inj. of Microspheres | | (Inj. Site) | |
| After 1 Week | 0.16 | 10.6 ± 3.0 (7.8–17.5) | 8.0 ± 1.1 (6.0–9.5) |
| 2 Weeks | 0.29 | 23.8 ± 18.5 (10.3–0.5) | 14.1 ± 7.2 (6.7–27.9) |
| 3 Weeks | 0.20 | 7.2 ± 0.9 (5.8–8.7) | 5.1 ± 1.4 (3.7–7.7) |
| 4 Weeks | 0.59 | 7.6 ± 3.0 (4.2–13.1) | 7.6 ± 0.8 (6.1–8.9) |

*[a]; n = 6  [b]; n = 9

A comparative analysis of the data in Table 1 clearly shows that delivery of ofloxacin with a single intraprostatic injection yields superior treatment results than oral delivery. Prostatic tissue concentrations of ofloxacin were maintained during 4 weeks at a slightly higher level through intraprostatic injection, than that achieved with oral administration. Additionally, levels of ofloxacin found in the serum after delivered by intraprostatic injection minute compared to oral administration. As a result, the method of this invention provides slightly more effective therapeutic results than conventional oral therapy with a dose that was about 1000 times smaller.

Example 15

After fixation of the prostate tissue in distilled water containing 10% formaldehyde solution, the specimens were dehydrated with and increasing concentration of ethanol, infiltrated with xylene, embedded in paraffin, and thinly sliced into 4 $\mu$m portions. These slices were then stained with Hematoxylin and Eosin then viewed under a microscope. Only moderate inflammation of the tissue was observed which can be accounted for as normal foreign body response.

In Vivo Evaluation of Minocycline HCl Loaded Microspheres 4 healthy male mongrel dogs of about 24 months old, and body weight of about 30 kg were used for in vivo evaluation of minocycline HCl loaded microspheres.

Example 16
Intraprostatic Injection of Microspheres 50 mg of the minocycline HCl microspheres fabricated by the method illustrated in method 3 above, were intraprosatically injected into the prostates of the above mentioned 4 dogs. Sampling of the prostate was performed 1, 2, 3, and 4 week intervals following the injection. Methods of injection administration, prostate collection, and tissue analysis were all the same as those used in example 13 above.

Example 17
Histopathological Analysis

The method of preparing histopathological slides was the same as that illustrated in Example 15 above. Compared with example 15, sever inflammation was observed and signs of tissue necrosis was evident in the week 2 samples.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements. Thus, while the present invention has been shown in the drawings and fully described above with particularity and detail in connection with what is presently deemed to be the most practical and preferred embodiment(s) of the invention, it will be apparent to those of ordinary skill in the art that numerous modifications, including, but not limited to, variations in size, materials, shape, form, function and manner of operation, assembly and use may be made without departing from the principles and concepts set forth herein.

What is claimed is:

1. A method for treating prostate diseases and disorders comprising the steps of:
   a) selecting at least one therapeutically effective substance for treatment of the prostatic disease or disorder;
   b) combining a therapeutically effective amount of said at least one therapeutically effective substance with a biodegradable polymer to create a treatment composition;
   c) forming said treatment composition into microspheres;
   d) suspending said microspheres in a liquid;
   e) placing said microsphere containing liquid in a syringe; and
   f) injecting said microsphere containing liquid directly into a prostate gland through a transurethral, transrectal, or transperineal route, such that the therapeutically effective substance is delivered to the prostate at a sustained rate as said microspheres biodegrade.

2. The method of claim 1 wherein said biodegradable polymer is an aliphatic polyester of a hydroxy acid.

3. The method of claim 2 wherein said aliphatic polyester of hydroxy acid is a member selected from the group consisting of: polylactic acid(L,DL), polyglycolic acid, poly (lactic-co-glycolic) acid, poly(orthoesters), poly(p-dioxanone), poly(alpha hydroxy butyric acid), and their copolymers with polyethylene oxide or polypropylene oxide, and mixtures thereof.

4. The method of claim 1 wherein said at least one therapeutically effective substance is a member selected from the group consisting of: antibiotics, anti-inflammatory drugs, α-blockers, 5 α-reductases, cytotoxic drugs, anti-angiogenetic drugs, anti-cancer drugs, and mixtures thereof.

5. The method of claim 4 wherein said therapeutically effective substance comprises about 10% to 50% w/w of the treatment composition.

6. The method of claim 1 wherein said formed microspheres are about 1 $\mu$m to 100 $\mu$m in size.

7. The method of claim 1 wherein said liquid further comprises at least one pharmaceutically acceptable excipient, such that drug stability and drug release profile control of the incorporated microspheres are increased.

8. The method of claim 1 wherein said liquid further comprises a substance having sol-gel transition properties.

9. The method of claim 8 wherein said liquid is a solution before injection, and a gel in human body temperature such that when injected, the liquid solution turns into a gel immediately upon entry into the human body and inhibits microsphere disbursement.

10. The method of claim 1 wherein a complete treatment is administered in a single injection.

11. The method of claim 1 wherein a complete treatment is administered in a series of injections.

12. The method of claim 11 wherein said series of injections are administered as needed until a desired therapeutic result is obtained.

13. The method of claim 1 wherein said prostatic disease or disorder is prostatitis, and said at least one therapeutically effective substance is a member selected from the group consisting of: antibiotics, anti-inflammatory drugs, and mixtures thereof.

14. The method of claim 1 wherein said prostatic disease or disorder is benign prostatic hypertrophy, and said at least one therapeutically effective substance is a member selected from the group consisting of: α-blockers, 5 α-reductase, cytotoxic drugs, anti-angiogenetic drugs, and mixtures thereof.

15. The method of claim 1 wherein said prostatic disease or disorder is prostate carcinoma, and said at least one therapeutically effective substance is an anticancer drug.

16. The method of claim 15 wherein said anticancer drug is a member selected from the group consisting of: alkylating agents, cytotoxic antibiotics, steroid hormones, vinca alkaloids, anti-angiogenetic agents, and mixtures thereof.

17. A method for treating prostatitis comprising the steps of:
   a) selecting at least one therapeutically effective substance for the treatment of prostatitis from the group consisting of antibiotics, anti-inflammatory drugs, and mixtures thereof;
   b) selecting a biodegradable polymer from the group consisting of: polylactic acid (L, DL), polyglycolic acid, poly(lactic-co-glycolic) acid, poly(orthoesters), poly(p-dioxanone), poly(alpha hydroxy butyric acid), and their copolymers with polyethylene oxide or polypropylene oxide, and mixtures thereof;
   c) combining a therapeutically effective amount of the chosen at least one therapeutically effective substance with the chosen biodegradable polymer to create a treatment composition;
   d) forming said treatment composition into microspheres ranging in size from about 1 um to 100 um;
   e) suspending said microspheres in about 1 to 5 ml of a sterile diluent which may contain pharmaceutically acceptable excipients for increasing drug stability and drug release control;
   f) agitating said microsphere containing diluent to obtain a uniform distribution of said microspheres throughout said liquid;
   g) placing said microsphere containing diluent in a syringe;
   h) injecting said microsphere containing diluent directly into a prostate gland through a transurethral, transrectal, or transperineal route, such that the therapeutically effective substance is delivered to the prostate at a sustained rate as said microspheres biodegrade and;
   i) re-administering injections of the microsphere containing diluent at chosen intervals for as long a duration as needed until a desired therapeutic result is obtained.

18. The method of claim 17 wherein said sterile diluent is a liquid solution before injection, and a gel at human body temperature such that when injected, the liquid solution turns into a gel immediately upon entry into the human body and inhibits microsphere disbursement.

19. A method for treating benign prostatic hypertrophy comprising the steps of:
   a) selecting at least one therapeutically effective substance for the treatment of benign prostatic hypertrophy from the group consisting of: α-blockers, 5 α-reductase, cytotoxic drugs, anti-angiogenetic drugs, and mixtures thereof;
   b) selecting a biodegradable polymer from the group consisting of polylactic acid (L, DL), polyglycolic acid, poly(lactic-co-glycolic) acid, poly(orthoesters), poly(p-dioxanone), poly(alpha hydroxy butyric acid), and their copolymers with polyethylene oxide, polypropylene oxide, and mixtures thereof,
   c) combining a therapeutically effective amount of the chosen at least one therapeutically effective substance with the chosen biodegradable polymer to create a treatment composition;
   d) forming said treatment composition into microspheres ranging in size from about 1 um to 1 00 um;
   e) suspending said microspheres in about 1 to 5 ml of a sterile diluent containing pharmaceutically acceptable excipients for increasing drug stability and drug release control;
   f) agitating said microsphere containing diluent to obtain a uniform distribution of said microspheres throughout said liquid;
   g) placing said microsphere containing diluent in a syringe;
   h) injecting said microsphere containing diluent directly into a prostate gland through a transurethral, transrectal, or transperineal route, such that the therapeutically effective substance is delivered to the prostate at a sustained rate as said microspheres biodegrade and;
   i) re-administering injections of the microsphere containing diluent at chosen intervals for as long a duration as needed until a desired therapeutic result is obtained.

20. The method of claim 19 wherein said sterile diluent is a liquid solution before injection, and a gel at human body temperature such that when injected, the liquid solution turns into a gel immediately upon entry into the human body and inhibits microsphere disbursement.

21. A method for treating prostate carcinoma comprising the steps of:
   a) selecting at least one therapeutically effective substance for the treatment of prostate carcinoma;
   b) selecting a biodegradable polymer from the group consisting of: polylactic acid (L, DL), polyglycolic acid, poly(lactic-co-glycolic) acid, poly(orthoesters), poly(p-dioxanone), poly(alpha hydroxy butyric acid), and their copolymers with polyethylene oxide, polypropylene oxide, and mixtures thereof;
   c) combining a therapeutically effective amount of the chosen at least one therapeutically effective substance with the chosen biodegradable polymer to create a treatment composition;
   d) forming said treatment composition into microspheres ranging in size from about 1 um to 100 um;
   e) suspending said microspheres in about 1 to 5 ml of a sterile diluent containing pharmaceutically acceptable excipients for increasing drug stability and drug release control;
   f) agitating said microsphere containing diluent to obtain a uniform distribution of said microspheres throughout said liquid;

g) placing said microsphere containing diluent in a syringe;

h) injecting said microsphere containing diluent directly into a prostate gland through a transurethral, transrectal, or transperineal route, such that the therapeutically effective substance is delivered to the prostate at a sustained rate as said microspheres biodegrade and;

i) re-administering injections of the microsphere containing diluent at chosen intervals for as long a duration as needed until a desired therapeutic result is obtained.

22. The method of claim 21 wherein said therapeutically effective substance is a member selected from the group consisting of: alkylating agents, cytotoxic antibiotics, steroid hormones, vinca alkaloids, anti-angiogenetic agents, and mixtures thereof.

23. The method of claim 22 wherein said sterile diluent is a liquid solution before injection, and a gel in human body temperature such that when injected, the liquid solution turns into a gel immediately upon entry into the human body and inhibits microsphere disbursement.

* * * * *